US008380270B2

(12) United States Patent
Menon

(10) Patent No.: US 8,380,270 B2
(45) Date of Patent: Feb. 19, 2013

(54) NON-INVASIVE OCULAR MONITORING

(75) Inventor: Naresh Menon, Pasadena, CA (US)

(73) Assignee: Chromologic LLC, Pasadena, CA (US)

( * ) Notice: Subject to any disclaimer, the term of this patent is extended or adjusted under 35 U.S.C. 154(b) by 483 days.

(21) Appl. No.: 12/694,208

(22) Filed: Jan. 26, 2010

(65) Prior Publication Data

US 2011/0184262 A1    Jul. 28, 2011

(51) Int. Cl.
*A61B 5/1455* (2006.01)
(52) U.S. Cl. ...................................................... 600/318
(58) Field of Classification Search ........... 600/318–321
See application file for complete search history.

(56) References Cited

U.S. PATENT DOCUMENTS

| | | | |
|---|---|---|---|
| 3,958,560 A | 5/1976 | March | |
| 3,963,019 A | 6/1976 | Quandt | |
| 4,166,695 A | 9/1979 | Hill et al. | |
| 4,836,207 A | 6/1989 | Bursell et al. | |
| 5,433,197 A | 7/1995 | Stark | |
| 6,370,407 B1* | 4/2002 | Kroeger et al. | 600/319 |
| 6,611,704 B1 | 8/2003 | van Best et al. | |
| 6,721,583 B1 | 4/2004 | Durkin et al. | |
| 6,885,882 B2* | 4/2005 | Cote et al. | 600/319 |
| 7,039,446 B2 | 5/2006 | Ruchti et al. | |
| 7,308,293 B2 | 12/2007 | Gerlitz | |
| 7,627,357 B2 | 12/2009 | Zribi et al. | |
| 2001/0029323 A1 | 10/2001 | Madarasz et al. | |
| 2001/0031914 A1* | 10/2001 | Gobeli et al. | 600/318 |
| 2003/0127609 A1 | 7/2003 | El-Hage et al. | |
| 2003/0233036 A1 | 12/2003 | Ansari et al. | |
| 2006/0094942 A1* | 5/2006 | Winther | 600/319 |
| 2006/0258918 A1 | 11/2006 | Burd et al. | |
| 2007/0078308 A1 | 4/2007 | Daly | |

OTHER PUBLICATIONS

International Search Report dated Mar. 30, 2010 for corresponding application No. PCT/US2010/022900, 1 sheet.
Written Opinion of the International Searching Authority, dated Mar. 30, 2010 for corresponding application No. PCT/US2010/022900, 6 sheets.
Cheuvront, Ph.D., et al., *Hydration Assessment of Athletes*, Sports Science Exchange, vol. 18, 2005, No. 2, 6 pages.
*Hydration Assessment of Athletes "WUT" Is the Answer?*, Sports Science Exchange, 2005, vol. 18, No. 2, 2 pages.
Gaasterland et al., *Rhesus monkey aqueous humor composition and a primate ocular perfusate*; Invest. Ophthalmol. Visual Sci., Nov. 1979, pp. 1139-1150.
Davson et al., *The Effect of Acetazoleamide on the Chemical Composition of the Aqueous Humour and Cerebrospinal Fluid or Some Mammalian Species and on the Rate of Turnover of* $^{24}$ NA in These Fluids, Journal of Physiology, 1957, 18 pages.
Madsen et al., "Optical Filter Design and Analysis: A Signal processing Approach", (*Digital Filter Concepts for Optical Filters*), pp. 95-165. International Search Report dated Mar. 30, 2010 issued in application No. PCT/US2010/022899, 2 pages.
Written Opinion of the International Searching Authority dated Mar. 30, 2010 issued in application No. PCT/US2010/022899, 5 pages.

* cited by examiner

*Primary Examiner* — W. B. Perkey
(74) *Attorney, Agent, or Firm* — Christie, Parker & Hale, LLP

(57) ABSTRACT

A device for measuring an analyte concentration level in a subject. The device includes: a light source configured for illuminating at least a portion of an anterior region of an eye of the subject with incident light having a substantially broad illumination spectrum at an angle substantially tangential to the surface of the eye; an optical collector configured for detecting reflected light from the at least a portion of the anterior region of the eye; an analyzer configured for analyzing the detected reflected light; and a processor configured to determine the analyte concentration level in the subject based on the analyzed reflected light.

20 Claims, 12 Drawing Sheets

NON-INVASIVE OCULAR MONITORING

FIELD OF THE INVENTION

The disclosure relates generally to ocular diagnosis, and, more particularly, to a non-invasive method and device for determining health condition of a subject through measurements of concentrations of analytes in the eye.

BACKGROUND

The Blood-Aqueous Barrier ("BAB") is a metabolic or cellular structure in the anterior chamber of the eye ("ACE") that restricts the passage of various chemical substances and microscopic objects, such as bacteria, between the bloodstream and the ACE tissue itself, while still allowing the passage of substances essential to metabolic function, such as oxygen, sodium and potassium salts and glucose. During duress, which may include traumatic injury, radiation exposure or diseases, such as cancer, the normal function of the BAB is adversely affected and results in a range of typically locally blocked analytes crossing into the anterior chamber of the eye. As such, detection of such analytes in the human eye can be a reliable indicator of a person's health.

In addition to monitoring the analytes that cross the BAB during injury or disease, the monitoring of analytes that cross the BAB during normal conditions may also indicate the health condition of a subject. For example, a sufficiently hydrated person typically has a specific concentration range of sodium salts (natremia), and the ability to detect raised or lowered concentrations of these sodium salts may provide a reliable indication of a person's hydration level. On the one hand, some of the methods typically used for accurately determining the hydration status, such as Total Body Water ("TBW") measurements and invasive measurements of plasma osmolality, are complex and require a clinical setting. Similarly, in addition to monitoring salts, monitoring of optically active carbohydrates, such as blood sugar (or glucose), can be performed in order to determine the glycemic condition of a person and their probability of becoming diabetic. However, the techniques available are invasive, inconvenient and often painful, which may lead to a high degree of inadequate treatment.

On the other hand, some of the more rapid and non-invasive techniques, such as bioimpedence measurements made through the skin using weak electrical currents, salivary osmolality measurements (for hydration), and monitoring physical signs of dehydration or diabetes, require baseline characterizations and may not be very specific. Additionally, non-invasive measurement modalities that require electromagnetic/optic probing made through the skin are easily corrupted by skin temperature, perspiration and body position of the subject, therefore limiting their application. Further, many of the non-invasive methods measure the concentration of analytes in the eye using laser assisted measurements of absorption at a select few wavelengths.

SUMMARY

One illustrative embodiment of the disclosure provides a device for accurately measuring an analyte concentration level in the aqueous humor by spectroscopic analysis of the reflected/scattered light using a broadband continuous wavelength visible light source (200 nm to 900 nm). Herein, a radiation source illuminates an anterior region of the eye of the subject with a substantially broad spectrum at an angle substantially tangent to the eye. The reflected and scattered radiations are collected and analyzed to obtain a characteristic spectrum of the detected scattered and reflected radiations. The characteristic spectrum is a combination of the light absorbed and scattered by the analyte based on its refractive index, size of the analyte, natural optical absorption, as well as its optical activity. This characteristic spectrum is then compared with a reference characteristic spectrum to compute the analyte concentration. Illumination at a tangential angle may avoid the total internal reflection characteristics of the eye and enable light collection normal to the corneal surface. Analysis with a broad illumination spectrum enables the determination of the optical properties of the analyte over a large response region.

An optical collector is configured for detecting an amount of scattered and reflected radiations from the anterior region. An analyzer is configured for analyzing the detected scattered and reflected radiations obtained, and a processor is configured for comparing the characteristic spectrum of the detected scattered and reflected radiations with a reference characteristic spectrum to compute the analyte concentration.

In various embodiments of the disclosure, split-beam polarization analysis of optical activity in the aqueous humor using incoherent illumination is performed with substantially the same optical source/receiver arrangement, but with the addition of polarization measuring optical components to quickly and accurately measure an optically active analyte.

In one embodiment of the present invention, the analyte concentration is measured by a non-invasive method using optical reflection spectroscopy. Here, measurements are rapid since the method is passive and the analyte is not excited optically with a coherent or monochromatic source. This method is reliable for diagnosis and does not require any baseline measurement. In addition, a broad illumination spectrum primarily in the visible light range is used and hence the device is cost effective, and easy to operate.

An embodiment of the present invention provides a device for measuring an analyte concentration level in a subject, the device including: a light source configured for illuminating at least a portion of an anterior region of an eye of the subject with incident light having a substantially broad illumination spectrum at an angle substantially tangential to the surface of the eye; an optical collector configured for detecting reflected light from the at least a portion of the anterior region of the eye; an analyzer configured for analyzing the detected reflected light; and a processor configured to determine the analyte concentration level in the subject based on the analyzed reflected light.

The processor may determine a health condition of the subject based on the analyte concentration level and reference data, and wherein the reference data corresponds to an analyte concentration level in an anterior region of a healthy eye.

The illumination spectrum may include wavelengths ranging from about 200 nm to about 900 nm.

The angle at which the eye is illuminated may range from about 70 degrees to about 90 degrees.

The device may further include a modulator configured for modulating the incident light to reduce extraneous effects.

The analyzer may include an optical spectrometer or an interferometer.

The light source may include an incoherent light source.

The analyte concentration level measured may be of an analyte comprising at least one of metabolic compounds selected from the group comprising: carbohydrates, sodium, sodium based salts, sugars, glucose, proteins, peptides, amino acids, fats, fatty acids, triglycerides, polysaccharides, alcohols, ethanol, toxins, hormones, vitamins, bacteria-related substances, fungus-related substances, virus-related substances, parasite-related substances, pharmaceutical compounds, non-pharmaceutical compounds, pro-drugs, drugs, precursors, metabolites, degradation products, biomarkers, and surrogate markers.

Another embodiment of the present invention may provide a method for measuring an analyte concentration level in a subject, the method including: irradiating at least a portion of an anterior region of an eye with incident light having a substantially broad illumination spectrum at an angle substantially tangential to the surface of the eye; detecting reflected light from the at least a portion of the anterior region; analyzing the reflected light; and determining the analyte concentration level based on the analyzed reflected light.

The method may further include determining a health condition of the subject based the analyte concentration level and reference data, wherein the reference data corresponds to an analyte concentration level in the anterior region of a healthy eye.

Another embodiment of the present invention provides a device for measuring an analyte concentration level in a subject, the device including: a light source configured for illuminating at least a portion of an anterior region of an eye of the subject with incident light having a substantially broad illumination spectrum at an angle substantially tangential to the surface of the eye; an optical splitter configured for splitting the incident light into first polarized rays and second polarized rays, wherein a polarization of the first polarized rays is substantially perpendicular to a polarization of the second polarized rays; a first polarization rotation element configured for rotating the polarization of the first polarized rays to be substantially parallel to the polarization of the second polarized rays; a first variable rotator configured for rotating the polarization of the first polarized rays and the polarization of the second polarized rays; a second variable rotator configured for rotating a polarization of first reflected rays and a polarization of second reflected rays, wherein the first reflected rays and the second reflected rays are reflected from the at least a portion of the anterior region of eye; a second polarization rotation element configured for rotating the polarization of the second reflected rays to be substantially perpendicular to the polarization of the first reflected rays; an optical combiner configured for combining first and second reflected rays into combined reflected rays; an optical collector configured for detecting the combined reflected rays; an analyzer configured for analyzing the combined reflected rays; and a processor configured to determine the analyte concentration level in the subject based on the analyzed combined reflected rays.

A path length of the second polarized rays and a path length of the second reflected rays in the aqueous humor may be greater than a path length of the first polarized rays and a path length of the first reflected rays, respectively, in the aqueous humor.

BRIEF DESCRIPTION OF THE DRAWINGS

Various embodiments of the invention will hereinafter be described in conjunction with the appended drawings provided to illustrate and not to limit the invention, wherein like designations denote like elements, and in which:

FIG. 1b illustrates the ray paths from the device in an eye according to FIG. 1a;

DETAILED DESCRIPTION

The detailed description set forth below in connection with the drawings is intended as a description of embodiments of a non-invasive method and device for determining health condition of a subject through measurements of concentrations of analytes in the eye in accordance with the present invention and is not intended to represent the only forms in which the invention may be constructed, or utilized. It is to be understood that the same or equivalent functions and structures may be accomplished by different embodiments that are also intended to be encompassed within the spirit and scope of the invention. As denoted elsewhere herein, like element numbers indicate like elements or features.

An embodiment of the present invention provides a device and a method for non-invasively measuring concentration of an analyte in the human eye.

More specifically, an embodiment of the present invention provides a device for accurately measuring an analyte concentration level in the aqueous humor in the ACE by spectroscopic analysis of the reflected (or scattered) light using a broadband continuous wavelength illumination source (or a substantially broad illumination source). For example, the illumination source may have an illumination spectrum from about 200 nm to about 900 nm. Here, the illumination source illuminates the ACE (or anterior region of the eye) of the subject with light at an angle substantially tangent to the eye. It should be appreciated that the anterior region for purposes of the present disclosure is defined generally as the region between the pupil and the cornea that encompasses the aqueous humor. The reflected light is collected and analyzed to obtain a reflected spectrum of the detected reflected light. This reflected spectrum is then compared with a reference spectrum to determine the analyte concentration.

The reference spectrum is prepared by in-vivo analysis. For example, reference spectra may be determined for different colored eyes or taking into account other physical parameters, such as corneal thickness.

Illumination at the tangential angle may substantially avoid total internal reflection within the eye, entry of light into the posterior chamber of the eye leading to substantial loss of light, and potential damage to the retinal region. Further, tangential illumination enables light collection normal to the corneal surface.

Figure 1A:
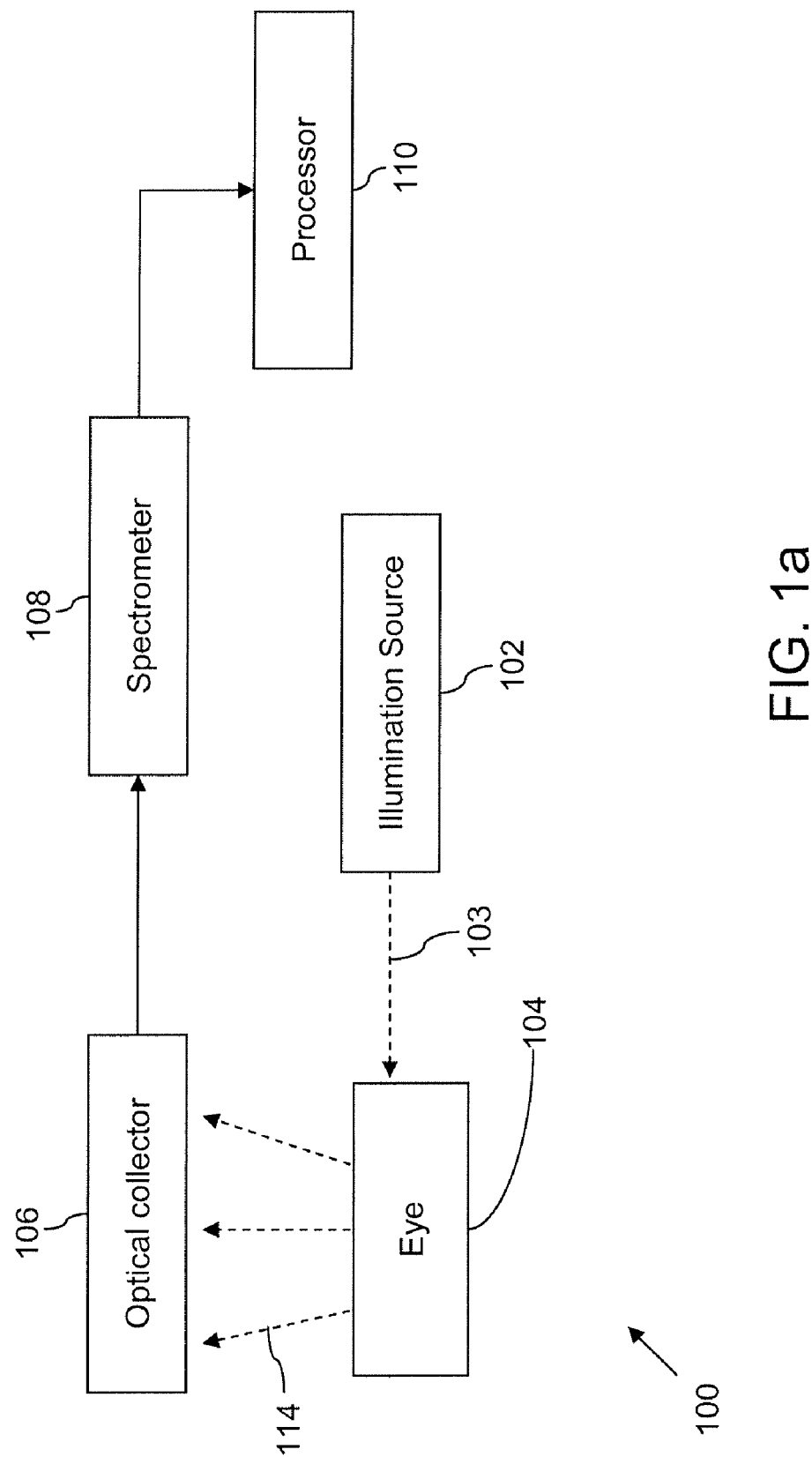
FIG. 1a illustrates a block diagram of a device for measuring analyte concentration level according to an embodiment of the present disclosure.

A device 100 for measuring at least one analyte concentration level in a subject according to an embodiment of the present invention is shown in FIG. 1a. The device 100 includes an illumination source (or optical illuminator) 102 for illuminating the ACE 104, and an optical collector 106 communicatively coupled to a spectrometer 108 configured for performing spectral analysis of the reflected light 114 from the eye 104. The device 100 also includes a processor 110 in communication with the spectrometer 108 and configured for determining the analyte concentration level.

The optical collector 106 can be coupled to the spectrometer 108 by using a data link, such as a fiber optic link. It should be appreciated that the optical collector 106 can be coupled to the spectrometer 108 by any other wired or wireless communication channels known to persons skilled in the art. Similarly, the spectrometer 108 can be communicatively coupled with the processor 110 with a wired or a wireless connection.

A standard illumination source may be a uniform visible light source with a halogen lamp, such as an ophthalmic slit lamp. A standard spectrometer may be a 2 nm grating or similar optically dispersive element, including holograms, coupled with a photodetector, such as a pixelated CCD array or photodiode array.

Figure 1B:
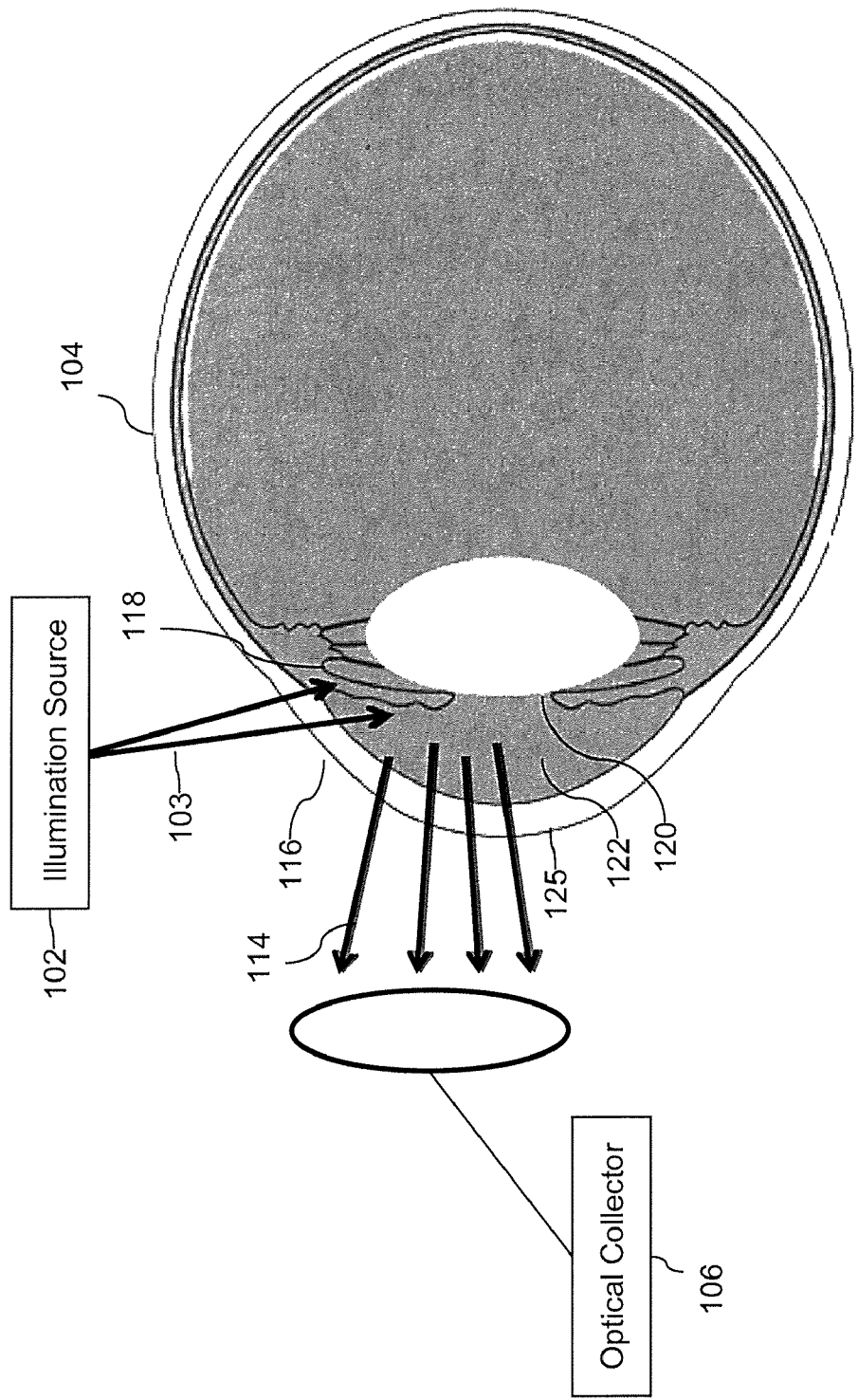

As illustrated in FIG. 1b, the eye 104 can be illuminated by the illumination source 102, such that incident light 103 is directed at an angle substantially tangential to the eye 104. In one embodiment, the incident light 103 is shaped with a combination of lenses such that it has a generally rectangular collimated profile.

The incident light 103 enters the cornea 116 and reflects off the iris 118. Therefore, a minimal amount of light enters the pupil 120. This increases the likelihood that only an anterior chamber 122 of the eye 104 is illuminated and the incident light 103 has a maximal path length in the anterior chamber 122 of the eye 104 where it traverses the aqueous humor.

The reflected light 114 from the anterior chamber 122 of the eye 104 is then collected by the optical collector 106 and further analyzed by the spectrometer 108 and processor 110 to determine the concentration of the analyte. It should be appreciated that reflected light 114 is collected from substantially uniform illumination of the anterior chamber 122.

The reflected light 114 from the eye 104 is collected by the optical collector 106, for example, a collimating lens assembly. An example of a collimating lens includes the 74-DA Collimating Lens that consists of a single aspheric lens with a field-of-view (FOV) ~45°.

The spectrometer 108 performs an analysis, e.g., a spectral analysis, of the collected reflected light 114. For example, the spectrometer 108 may determine a reflected spectrum. The spectrometer 108 may, for example, be an optical spectrometer or an interferometer. The spectrometer 108 converts the reflected spectrum into electrical signals, which are analyzed by the processor 110. For example, the processor 110 may compare the reflected spectrum to a reference spectrum to determine an analyte concentration level in the aqueous humor.

Figure 8:
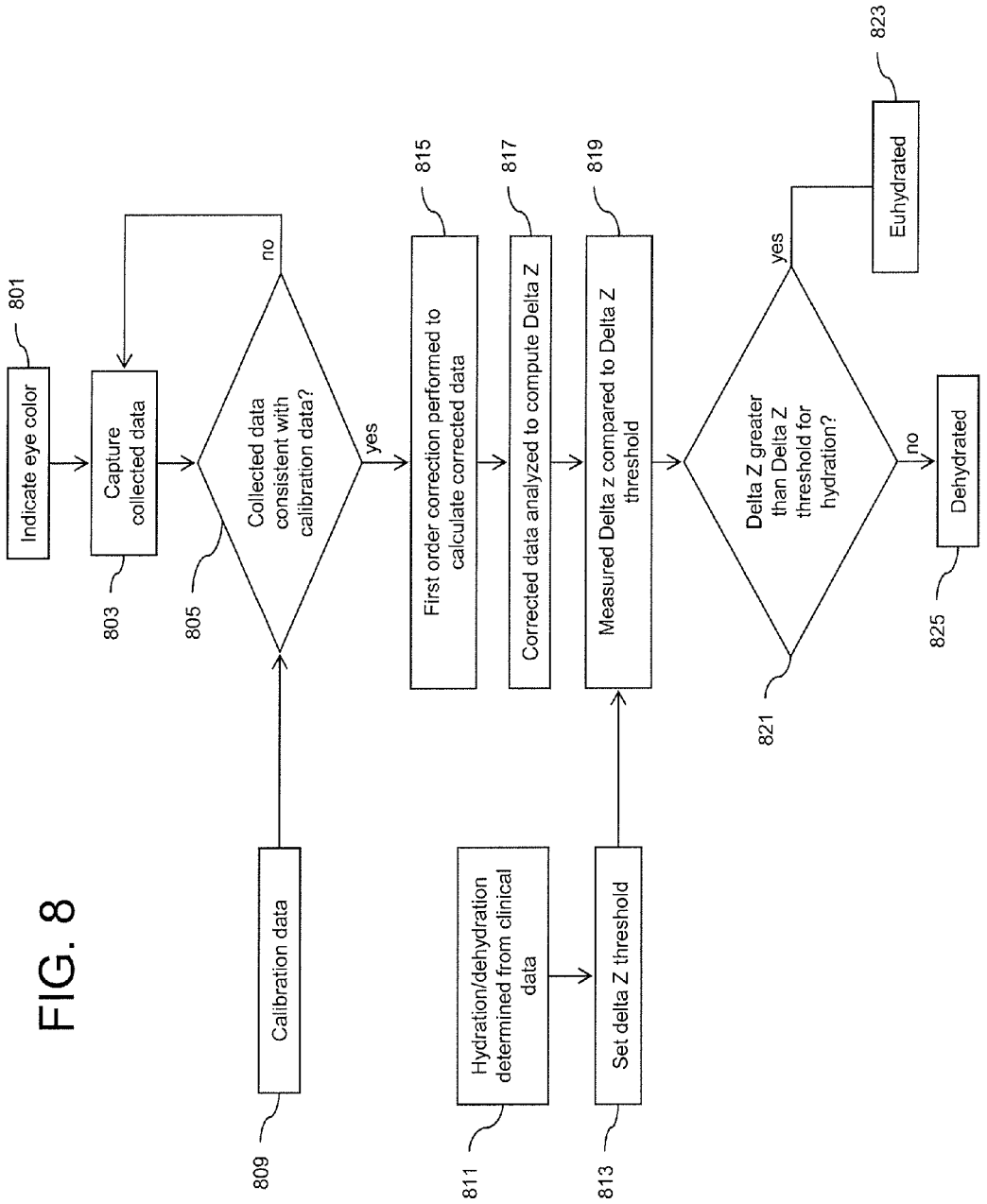
FIG. 8 is a flowchart illustrating a method for analyzing data to determine the hydration status of a subject according to an embodiment of the present invention.

An algorithm used to determine hydration status of a patient according to an embodiment of the present is illustrated in FIG. 8. Here, the user selects the approximate eye color of the test subject 801 based on broad color definitions, e.g., blue, green, brown or other similar categorization of the color of the iris. The reflected light 114 is captured 803 by the optical collector 106, analyzed by the spectrometer 108, and recorded by the processor 110 as collected data.

Calibration (or reference) data 809, including typical characteristics of light from the light source 103 that has been reflected from different colored irises, is stored in memory of the processor 110. Illumination source data, including the spectrum of the illumination source 102, is also stored in the memory of the processor 110. This calibration data may be parameterized values that include one or more spectral peaks, spectral full-width-at-half-maxima (FWHM), and spectral intensity.

The collected data is compared with the calibration data 805. If the collected data is not consistent with the calibration data, then the collected data is captured again. If the collected data is consistent with the calibration data, the processor 110 selects calibration data for further analysis that is consistent with the reflected light 114 coming from the iris 118, i.e., the iris of the selected color. Here, extraneous light from other regions of the eye, such as the sclera, pupil and eyelid, is rejected.

The collected data is further processed by performing a first order correction 815, where the calibration data and illumination source data are subtracted from the collected data. The resulting corrected data may, for example, be analyzed in the spectral region of about 400 nm to about 500 nm to compute a maximum deviation, Delta Z, from the calibration data 817. Data from clinical and laboratory experiments that empirically determines which values of Delta Z correspond to adequate hydration and which values of Delta Z correspond to dehydration are also stored in the processor. A Delta Z threshold for hydration, where values of Delta Z less than the Delta Z threshold correspond to dehydration and values of Delta Z greater than the Delta Z threshold correspond to euhydration (or adequate hydration), is compared with the computed Delta Z 821 to determine whether the Delta Z value is greater than the threshold for hydration 821. If the Delta Z value is less than the Delta Z threshold, then the subject is dehydrated or likely to be dehydrated 825. If the Delta Z value is greater than the Delta Z threshold, then the subject is adequately hydrated or likely to be adequately hydrated 823.

The reference spectrum and calibration data is obtained computing the concentration of different analytes in the eye using data obtained through measurements performed in clinical settings of humans and non-human primates subject to controlled and correlated variations of various analytes. Additional reference spectra that account for eye color, corneal thickness, and physical parameters of the eye that vary from individual to individual may also be included. The reference spectra are stored in a memory unit in the processor 110.

Figure 3:
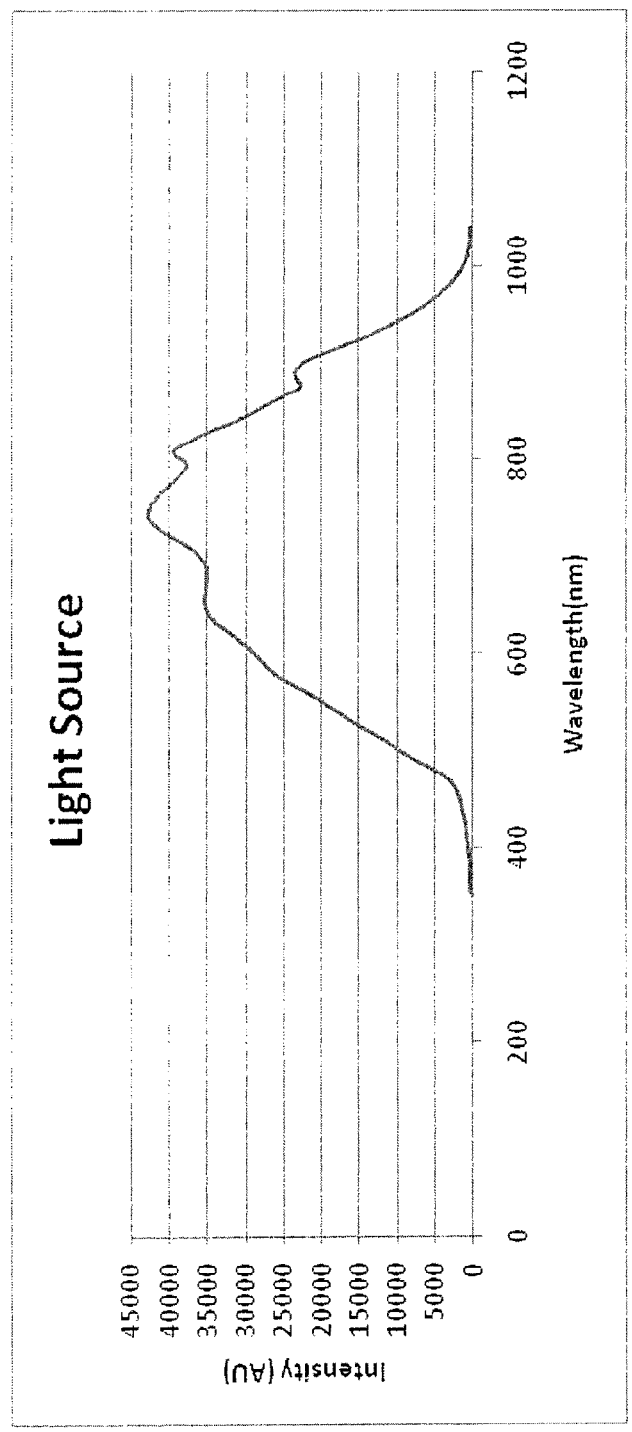
FIG. 3 is a graph that illustrates an illumination spectrum according an embodiment of the present disclosure.

In one embodiment, the illumination source 102 is a broadband continuous wavelength visible source that generates light having wavelengths in the range from about 200 nm to about 900 nm, and more specifically from about 300 nm to about 900 nm. It should be appreciated that the illumination source 102 can be an incoherent source and can generate non-polarized light. It should further be appreciated that the incident light may not be collimated. FIG. 3 is a graph illustrating an exemplary spectrum of the light generated by the illumination source. As illustrated, the wavelengths are in the range of about 300 nm to about 1000 nm.

In various embodiments of the present invention, the analyte is at least one of metabolic compounds, carbohydrates, sodium, sodium based salts, sugars, glucose, proteins, peptides, amino acids, fats, fatty acids, triglycerides, polysaccharides, alcohols, ethanol, toxins, hormones, vitamins, bacteria-related substances, fungus-related substances, virus-related substances, parasite-related substances, pharmaceutical compounds, non-pharmaceutical compounds, pro-drugs, drugs, and any precursor, metabolite, degradation product, biomarkers and surrogate markers. In another embodiment of the present invention, the osmolality of the aqueous humor is also determined.

Figure 5:
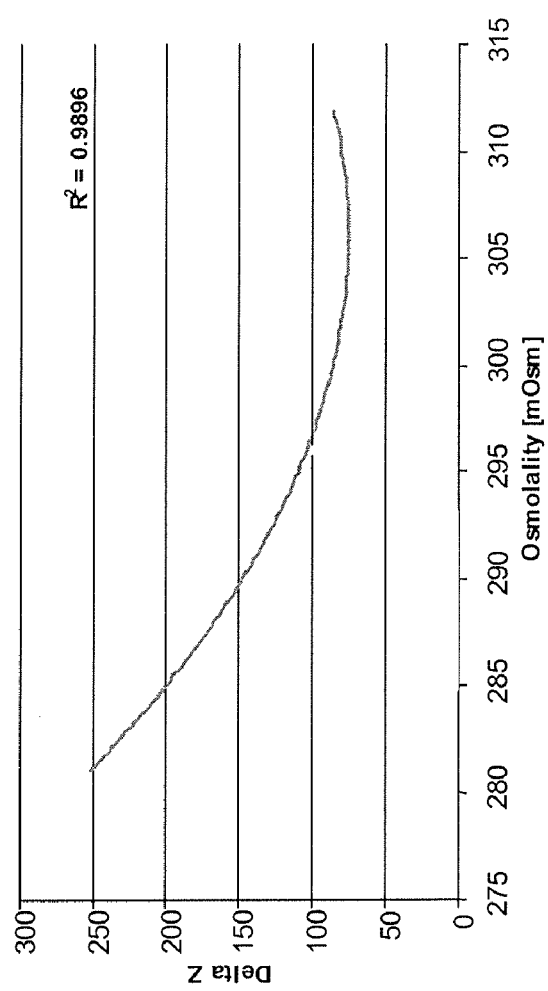
FIG. 5 is a graph of data from the device of FIG. 1 processed to determine aqueous humor osmolality.

In one embodiment of the present invention as shown in FIG. 1a, optical density of the aqueous humor is measured by reflection spectroscopy. FIG. 5 shows data that demonstrates a strong correlation between optical density of the aqueous humor obtained through the practice of the invention with corresponding osmolality changes of the aqueous humor. Measurements of osmolality are correlated to the amount of sodium based salts present in the human body. Lower values of Delta Z indicate lower levels of hydration.

Figure 6:
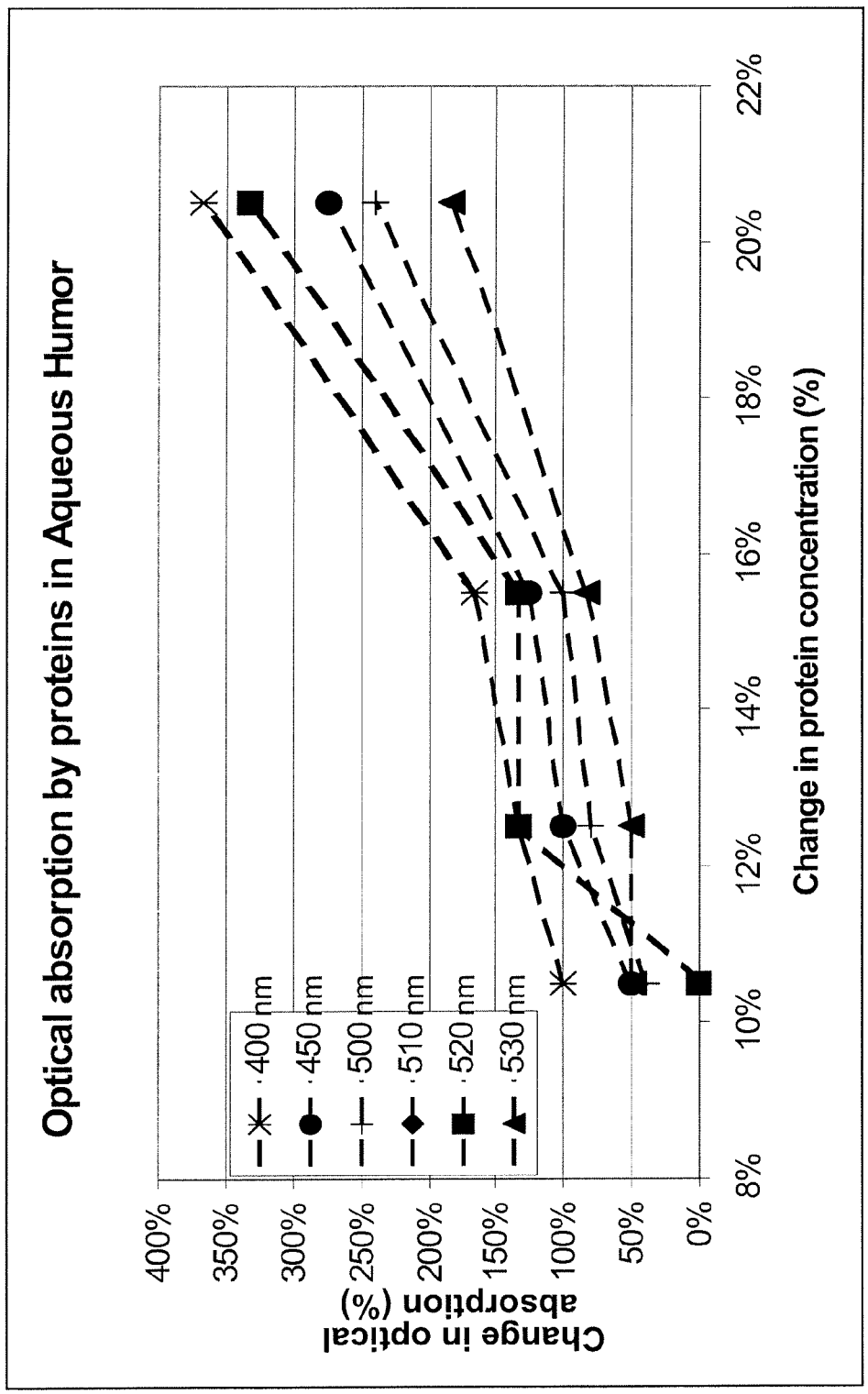
FIG. 6 is a graph of data from the device of FIG. 1 processed to determine aqueous humor optical absorption.

Another embodiment of the present invention includes the determining of the amount of proteins and cells present in the aqueous humor by measuring wavelength dependent optical absorption. FIG. 6 shows data that demonstrates a strong correlation between optical absorption obtained through the practice of the invention and protein concentration in the aqueous humor. Here, the change in optical absorption measured by the instrument at varying changes in protein concentration in the aqueous humor is shown for different wavelengths of incident light (e.g., 400 nm, 450 nm, etc). Measurements of protein concentration in the aqueous humor correlate to the extent of damage to the blood-eye-barrier by diseases, such as, but not limited to, malaria and cancer, as well as trauma, such as, but not limited to, traumatic brain injury, exposure to ionizing radiation and laser, and can also be used to gauge sudden changes in inter-ocular pressure (IOP) that often accompany eye/head trauma.

According to another embodiment of the present invention, modulators such as frequency modulators and phase modulators can be used along with spectrometer 108 and processor 110 to reduce extraneous effects. By modulating the illumination source, e.g., in phase and/or time, and synchronizing the measurement of the reflected light at the spectrometer, effects from noise, such as ambient light and intrinsic fluorescence, can be mitigated. Here, the source is modulated, and the receiver is synchronized to respond to a carrier wave represented by the modulation. The carrier wave modulation is then removed at the detector to extract the useful signal. Similarly, optical filters can be used with the optical collector 106 or illumination source 102 to filter and/or block radiation from extraneous sources.

Figure 2A:
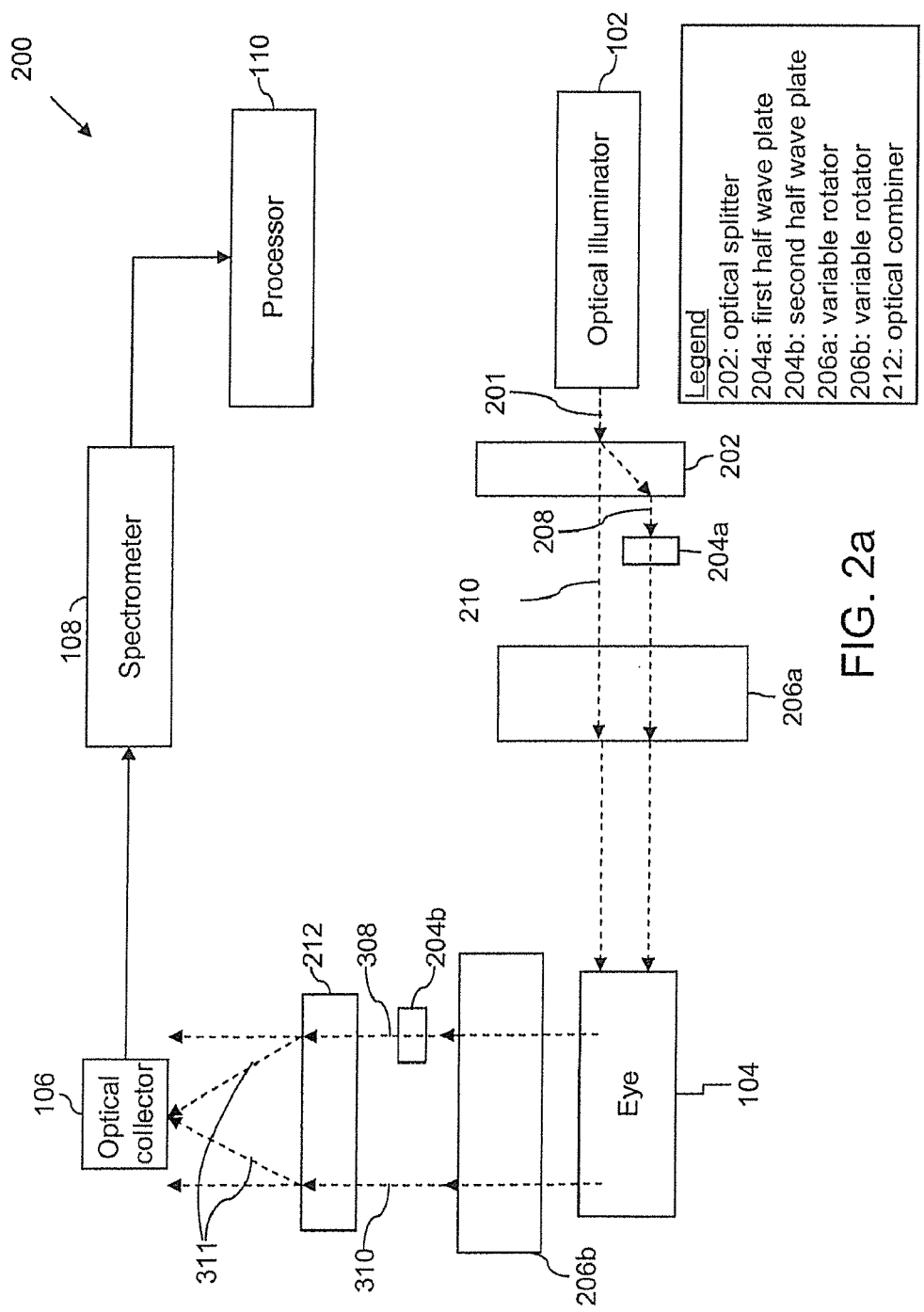
FIG. 2a illustrates a block diagram of a device for measuring an analyte concentration level according to another embodiment of the present disclosure.

A device 200 to measure an analyte concentration level in a subject according to another embodiment of the present invention is shown in FIG. 2a. As described with respect to FIG. 1a, the device 200 includes the illumination source (or optical illuminator) 102, and the optical collector 106 communicatively coupled to the spectrometer 108, which is configured for performing spectral analysis.

The device 200 can further include an optical splitter 202 for splitting the incident light 201 from the illumination source 102 into a first polarized ray 208 with a first polarization and a second polarized ray 210 with a second polarization perpendicular to the first polarization, and an optical combiner 212 for combining a first reflected ray 308 and a second reflected ray 310.

A first half wave plate 204a is positioned between the optical splitter 202 and the eye 104, and a second half wave plate 204b is positioned between the eye 104 and the optical combiner 212. The optical splitter 202 and the half wave plates 204a and 204b may be formed from any suitable birefringent materials, such as calcite and yttrium lithium fluoride.

The device 200 includes a first variable rotator 206a positioned between the optical splitter 202 and the eye 104 for rotating the polarization of the first and second polarized rays 208 and 210, and a second variable rotator 206b positioned between the eye 104 and the optical combiner 212 for rotating the first and second reflected rays 308 and 310. Variable rotators 206a and 206b can be made from a suitable optoceramic material, such as PLZT, lithium niobate or liquid crystals.

In operation, the optical splitter 202 splits the incident light 201 from the illumination source 102 along its polarization into a first polarized ray 208 and a second polarized ray 210. It should be appreciated that the illumination source 102 may be an incoherent source and may generate non-polarized light. The first polarized ray 208 and second polarized ray 210 may be perpendicular in polarization to each other. The first polarized ray 208 is further passed through a half wave plate 204a which rotates the polarization of the first polarized ray 208 by about 90 degrees.

Here, the first polarized ray 208 and second polarized ray 210 are polarized in same direction. The first and second polarized rays 208 and 210 then pass through the first variable rotator 206a to rotate the polarization. It should be appreciated that both rotators 206a and 206b can be biased by an external voltage supply to provide identical optical rotation, conjugate optical rotation where they cancel each other, or some combination of both.

As shown in equation 1, an illumination source split into its electric (E) and magnetic (Z*H) field components and travelling through a rotator experiences a complex phase shift $\phi$ that can be characterized by the matrix M.

$$\begin{bmatrix} E_{final} \\ ZH_{final} \end{bmatrix} = \begin{bmatrix} \cos\phi & \frac{j\sin\phi}{n} \\ jn\sin\phi & \cos\phi \end{bmatrix} \begin{bmatrix} E_{initial} \\ ZH_{initial} \end{bmatrix} = M \begin{bmatrix} E_{initial} \\ ZH_{initial} \end{bmatrix} \quad (1)$$

The phase shift $\phi$ is given by equation (2) where $\lambda$ is the wavelength of the light source, K is the Kerr coefficient of the material, n is the refractive index, E is the external electric field applied to the rotator, t is the thickness of the rotator and $\lambda_0$ is the characteristic wavelength of the Kerr material. It will be appreciated that a similar phase shift is possible with a Pockels material as well.

$$\phi = \left(\frac{2\pi}{\lambda}\right)\lambda_0 K E^2 t \quad (2)$$

After passing through the first variable rotator 206a the polarized rays are directed at a tangential angle to the eye 104. The first and second polarized rays 208, 210 are reflected from the iris 118 (or anterior portion) of the eye 104 at an angle substantially normal to the eye 104.

Figure 2B:
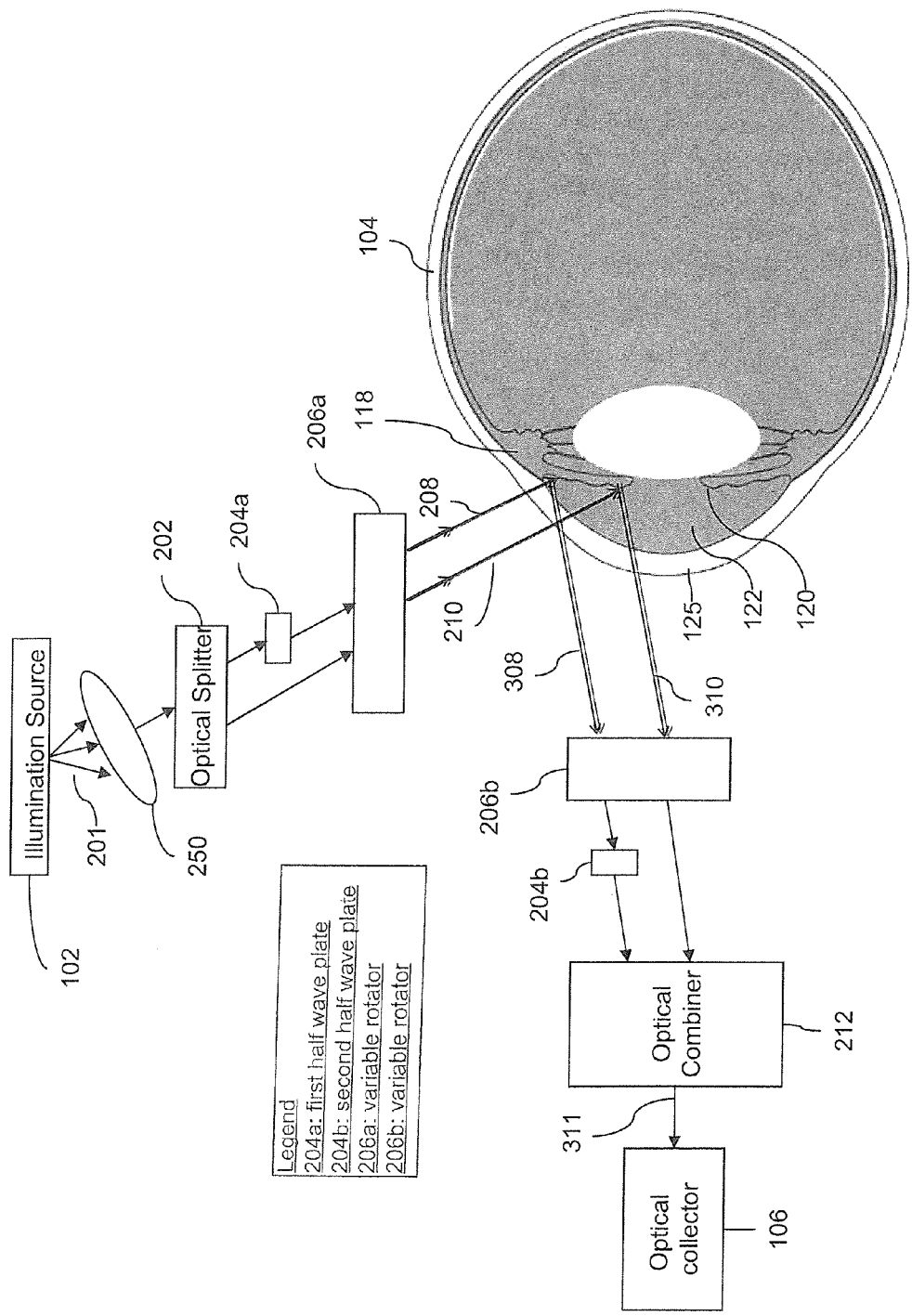
FIG. 2b illustrates the ray paths in an eye from the device according to FIG. 2a FIG. 2c illustrates a view of an eye with illumination points according to an embodiment of the present disclosure.
Figure 2C:
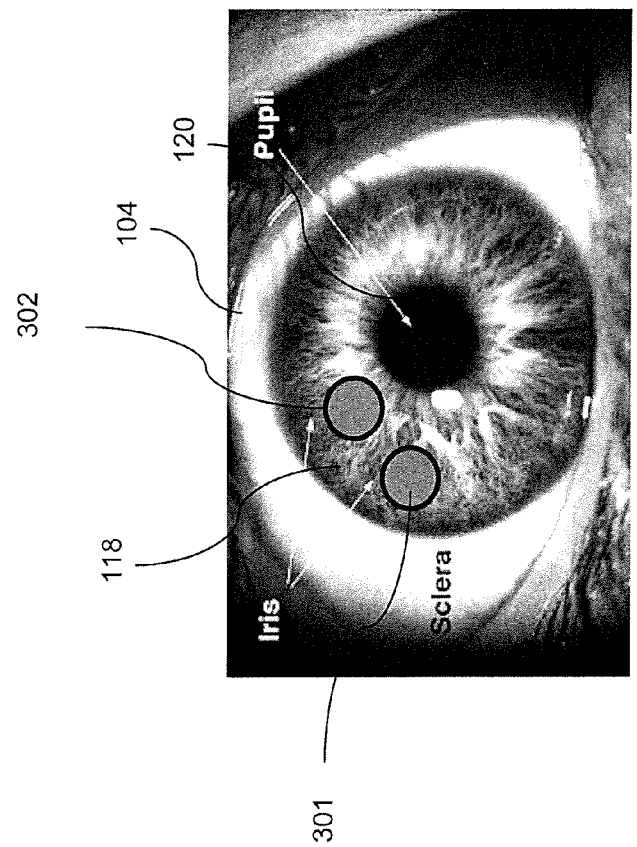
Figure 2C:
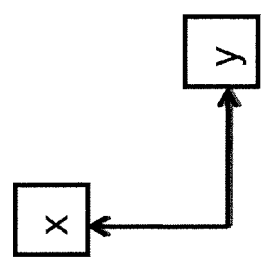

FIG. 2c is a drawing of the eye 104 showing a first spot 301, where the first polarized ray 208 illuminates the eye 104, and a second spot 302, where the second polarized ray 210 illuminates the eye 104.

After reflection from the eye 104, both first and second reflected rays 308 and 310 pass through the second variable rotator 206b. Here, the second variable rotator 206b may be synchronized with the first variable rotator 206a, or the second variable rotator 206b may act independently to provide a second polarization correction to the reflected light rays The first reflected ray 308 passes through a second half wave plate 204b, which rotates the polarization of the first reflected ray by about 90 degrees to be perpendicular in polarization to second reflected ray 310. Alternatively, the second reflected ray 310 could pass through a second half wave plate which rotates the polarization of second reflected ray 310 by about 90 degrees to be perpendicular in polarization to the first reflected ray 308.

The first reflected ray 308 and the second reflected ray 310 then pass through an optical combiner 212, which is configured to combine the first and second reflected rays 308, 310 along their polarization. In other words, the two orthogonally polarized first and second reflected rays 308, 310 are combined by the optical combiner 212 so that their polarization axes are aligned. The combined rays 311 from the optical combiner 212 are collected by the optical collector 106, for example, a collimating lens assembly.

Equation 1 can be applied to the optical rotation experienced by the each of the polarized and reflected rays 208, 210, 308, 310 as it travels through the birefringent analytes present in the aqueous humor where the phase shift φ is given by equation (3).

$$\phi = \left(\frac{2\pi}{\lambda}\right)\Delta nt \tag{3}$$

In equation 3, Δn is the change in refractive index from birefringence and t is the distance traveled by the light ray through the aqueous humor.

FIG. 2b is a ray diagram illustrating the path of the first and second polarized rays 208, 210 and the first and second reflected rays 308, 310, as described in the above. It should be appreciated that the incident light 201 can be collimated by a collimating lens assembly 250, and then split into the first and second polarized rays 208, 210. It should also be appreciated that each of the first and second polarized rays 208, 210 and the first and second reflected rays 308, 310, travels through the same tissue layers, specifically the cornea, which cancels out contributions from corneal birefringence and other first order effects.

It should be appreciated that while the optical paths of the two rays traverse the same tissues in the ACE, one of the rays traverses a greater distance through the aqueous humor than the other and is relatively more affected by a phase shift resulting from the optical activity of one or more analytes in the aqueous humor.

The first and second reflected rays 308, 310 reflected from the iris 118 of the eye 104 are combined by the optical combiner 212 to be combined reflected rays 311. The combined reflected rays 311 are then analyzed by the optical collector 106 and spectrometer 108.

From equation 1, the combined reflected rays 311 incident on the optical collector 106 may be expressed in terms of the matrix M and the refractive index of the incident medium $n_0$ and the refractive index of the collection medium $n_m$ given by equation (4). It will be appreciated that for most applications $n_0 = n_m = 1$ is a sufficiently accurate approximation where the incident and collection medium is air. $E^+$ and $E^-$ are the two polarization components of the light in each medium.

$$\begin{bmatrix} E_m^+ \\ E_m^- \end{bmatrix} = \begin{bmatrix} 1 & 1 \\ n_m & -n_m \end{bmatrix}^{-1} M_m \begin{bmatrix} 1 & 1 \\ n_0 & -n_0 \end{bmatrix} \begin{bmatrix} E_0^+ \\ E_0^- \end{bmatrix} = \begin{bmatrix} Q_{11} & Q_{12} \\ Q_{21} & Q_{22} \end{bmatrix} \begin{bmatrix} E_0^+ \\ E_0^- \end{bmatrix} \tag{4}$$

From equation 4, the percentage transmission of the combined reflected rays 311 incident on the optical collector 106, as a function of wavelength, is given by equation (5).

$$T(\lambda) = \frac{1}{Q_{11}(\lambda)} \tag{5}$$

Spectrometer 108 performs a spectral analysis of a reflected spectrum, or a portion of the reflected spectrum, of the combined reflected rays 311. The spectrometer 108 may be an optical spectrometer or an interferometer. The spectrometer 108 converts the reflected spectrum into electrical signals, which are analyzed by the processor 110. The processor 110 compares the reflected spectrum to a reference spectrum to determine an analyte concentration level in the aqueous humor. The reference electric signals corresponding to the reference spectrum are stored in a memory unit in the processor 110.

A substantial amount of light included in the combined reflected rays 311 is collected by the optical collector 106. In the absence of an analyte, the net rotation incurred by both the first and second polarized rays 208, 210 and both the first and second reflected rays 308, 310 will be zero. In the presence of an optically active analyte, such as glucose, birefringence of the eye 104 will change, resulting in different path lengths for the first and second polarized rays 208, 210 and the first and second reflected rays 308, 310. As a result, less then 100% of the light would be collected by optical collector 106.

Here, the optical combiner 212 that couples the first and second reflected rays 308, 310 into the combined reflected rays 311 has a narrow polarization acceptance region. If there is no optically active analyte in the anterior chamber 122, both the first and second polarized rays 208, 210 and both the first and second reflected rays 308, 310 experience no rotation of their polarization, and about (or almost) 100% of the incident light 103 will be collected at the optical collector 106 (except for nominal absorption from eye tissue). However, optically active material in the eye causes the second polarized rays 210 and the second reflected rays 310, which have longer path lengths through the anterior chamber 122, to undergo a greater polarization rotation. Therefore, the optical combiner 212 is not able to couple the first and second reflected rays 308, 310 completely, so that less than 100% of light is incident on the optical collector 106.

The second variable rotator 206b may be used to scan the polarization to determine whether there is a drop in intensity of the second reflected rays 310. The activity of the analyte may then be measured according to the value of the rotation and the intensity recorded.

The first variable rotator 206a rotates the polarization of the first and second polarized rays 208, 210 through different polarization values. These polarization values may be mapped either randomly along the Poincare phase space or through ordered polarization values. By monitoring the intensity of the combined reflected rays 311 and correlating the polarization setting of the second variable rotator 206a with this intensity, the net polarization effect of the active analytes in the aqueous humor may be calculated by determining the polarization setting of the second variable rotator 206a where the polarization walk-off between the first reflected rays 308 and the second reflected rays 310 is at a maximum. This may be determined by measuring the polarization setting where the intensity of the combined reflected rays 311 is at a minimum.

In embodiment of the present invention, the second variable rotator 206b may be used either in synchronization with the rotator 206a or independently. The second variable rotator 206b is designed to provide polarization correction as needed.

In an embodiment of the present invention, the light received by the optical collector 106 may be directly converted into a voltage measurement. Changing the rotation of the variable rotators 206a and 206b will rectify the decrease in light collected by optical coupler 106. The amount of rotation that occurs in the variable rotators 206a and 206b may provide a precise measurement of the birefringence at different wavelengths, and from this characteristic mapping of the birefringence, the concentration of optically active analyte in the presence of other birefringence contributors, such as the corneal shape, can be extracted.

Figure 7:
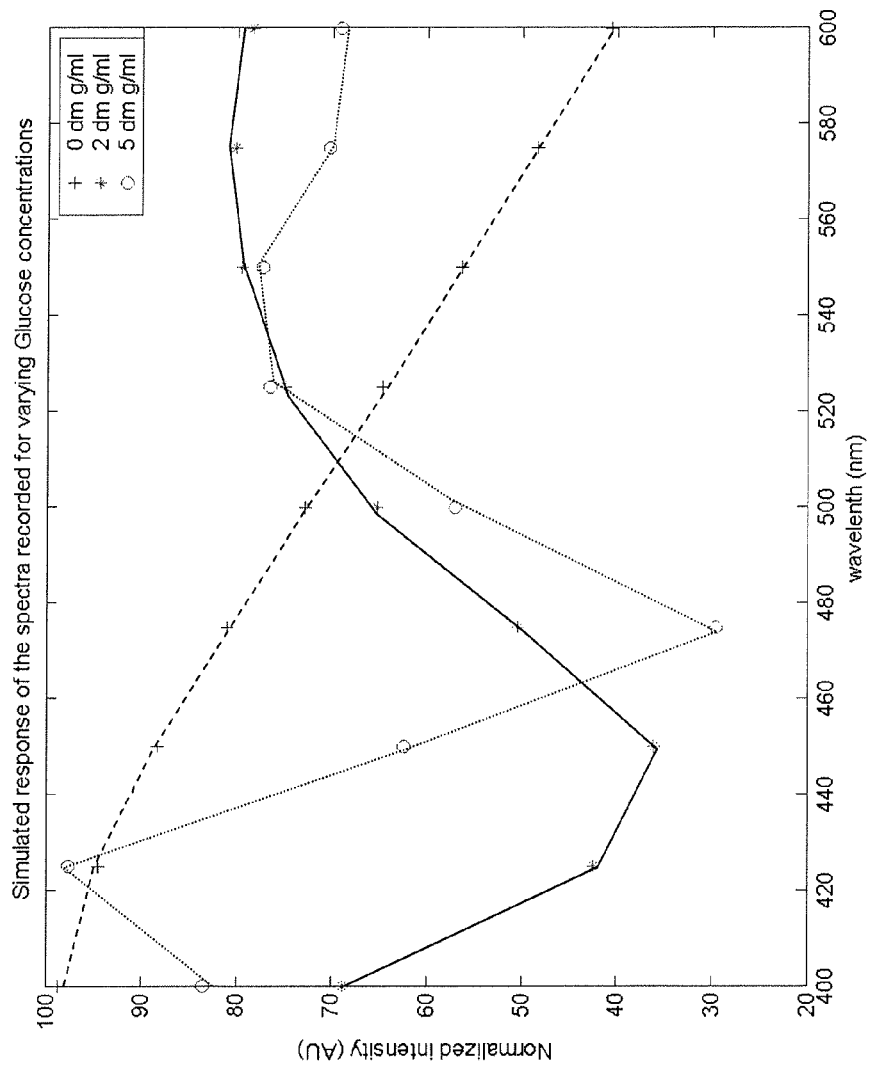
FIG. 7 is a graph of data from the device of FIG. 2 processed to determine aqueous humor analyte optical activity.

FIG. 7 shows the normalized intensity as a function of wavelength that would be measured at the spectrometer 108, as calculated from equation (5), for different concentration of glucose. FIG. 7 shows that different concentrations of optically active material, such as the different concentrations of glucose shown here, present in the aqueous humor of the eye result in a wavelength dependent response that is distinguished by various spectral parameters, including intensity at a particular wavelength, as well as the ratio of intensities at two or more wavelengths.

According to another embodiment of the present invention the sensitivity of the birefringence measurement can be increased by using filters with the illumination source to perform measurements at different wavelengths. This can be implemented by having various optical elements in parallel, or by serial measurements where different filters are inserted into the light path.

According to another embodiment of the present invention, a separate variable rotator may be provided for each of the first and second polarized waves for comparative measurements of different analytes.

As illustrated in the FIG. 2c, the first and second spots 301, 302 are located at different X and Y coordinate locations. It should be appreciated that the second polarized ray 210 and the second reflected ray 310, which is reflected from second spot 302 located closer to the pupil 120, travels a longer distance through the aqueous humor than the first polarized ray 208 and the second reflected ray 308, which is reflected from the first spot 301 located further from the pupil 120. This difference is essentially due to the curvature of the cornea 125 which has an apex at the pupil 120. It should be further appreciated that the first and second polarized rays 208, 210 are reflected by the iris 118.

In an embodiment of the present invention, wherein the device may be head mounted or configured to be integrated with eye wear.

Figure 4:
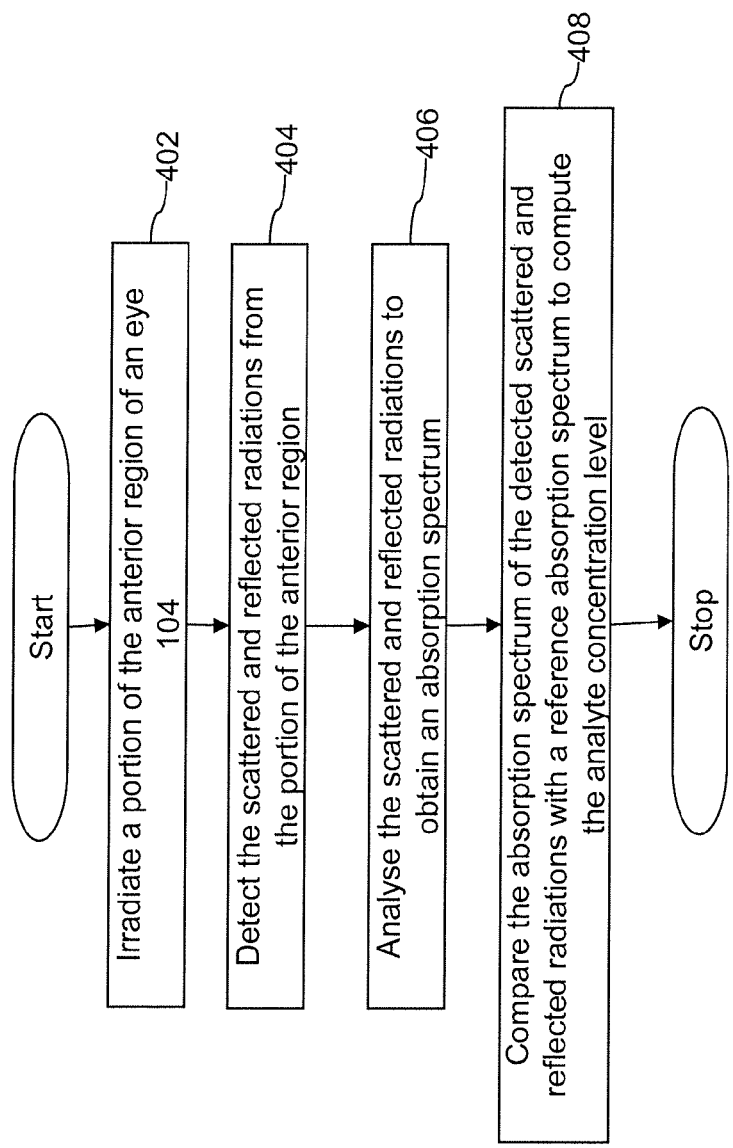
FIG. 4 is a flowchart illustrating a method for measuring an analyte concentration level in a subject according to an embodiment of the present disclosure.

FIG. 4 is a flowchart illustrating a method for measuring an analyte concentration level in a subject according to an embodiment of the present invention. At step 402, the anterior portion of an eye similar to eye 104 is illuminated at a tangential angle by a light source similar to light source 102. According to another embodiment of the invention, the angle at which the eye is illuminated is in the range of about 70 degrees to about 90 degrees.

At step 404, the reflected and scattered rays are captured by an optical collector similar to optical collector 106. Optical collector 106 is coupled to a spectrometer similar to spectrometer 108. At step 406, reflected and scattered light is analyzed by the spectrometer to obtain a characteristic spectrum. The spectrometer is connected to a processor similar to processor 110. At step 408, the processor compares the characteristic spectrum of the detected scattered and reflected radiations with a reference characteristic spectrum to compute the analyte concentration level. The comparison is performed using multivariable analysis and calibration techniques. The multivariate calibration techniques may include Classical Least Square (CLS), Inverse Least Square (ILS), Principal Component (PC) and Partial Least Square (PLS).

Figure 9:
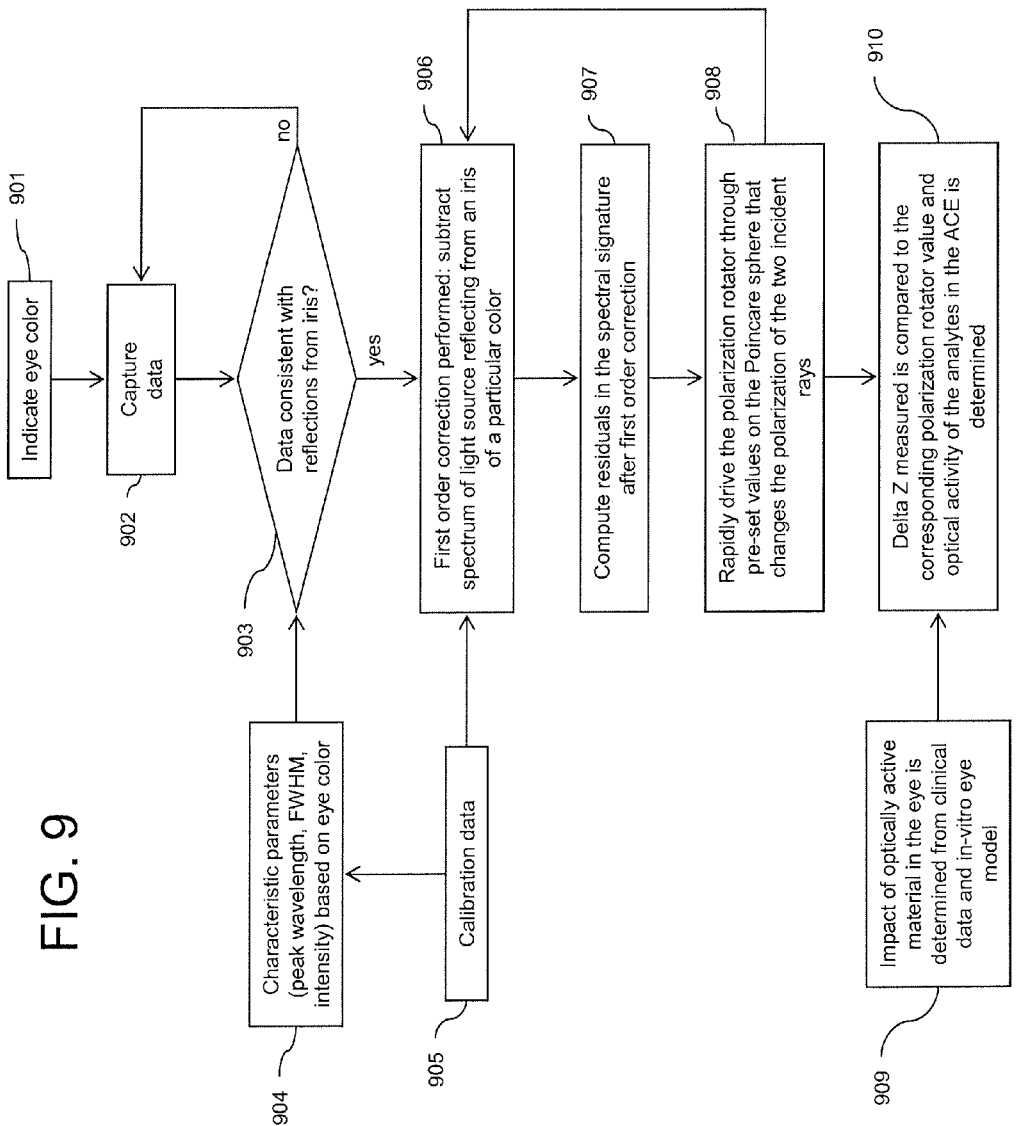
FIG. 9 is a flowchart illustrating a method for analyzing data to determine the concentration of an optically active analyte present in the ACE according to an embodiment of the present invention.

An algorithm used to determine concentrations of one or more analytes, such as glucose, based on their polarization effect according to an embodiment of the present invention is illustrated in FIG. 9. In this embodiment, the polarization of the incident rays is varied with a polarization rotator and the data collected is compared with the known values of concentrations of optically active analytes measured in clinical and in-vitro samples. From these known concentrations, the concentration of the optically active analyte in the subject eye may be determined.

As shown in FIG. 9, an operator of the device indicates the eye color of the subject 901. The device then captures the data 902. The device determines whether the data is consistent with reflections of the iris of the subject 903 based on calibration data 905 which may include characteristic parameters, such as peak wavelength, full-width at half-maximum (FWHM), and intensity, based on eye color 904. If the data is not consistent with reflections from the iris, then the device will again capture data 902.

If the data is consistent with reflections of the iris, then a first order correction is performed where the spectrum of the light source reflecting from an iris of a particular color, which is obtained from the calibration data 905, is subtracted from the captured data 906. Next, the device computes residuals in the spectral signature 907. For example, the magnitude of the residuals in the blue-green spectra (400-500 nm) may be called Delta Z. Then, the device rapidly drives one or more of the polarization rotators through pre-set values on the Poincare sphere that changes the polarization of the two incident rays 908. Steps 906, 907, and 908 may be repeated, for example, to further refine the captured data or to achieve a more accurate measurement value.

The Delta Z measured is then compared to the corresponding polarization rotator value and the optical activity of the analytes in the ACE is determined 910. Here, the impact of the optically active material in the eye may be determined from clinical data and/or in-vitro eye models 909.

The system and device as disclosed can be used to measure analytes that are designed to cross the BAB only during injury/disease—such as tripan-blue. By measuring the concentration of the analyte, the user is able to estimate the level of BAB damage/disruption and accordingly determine the extent of the disease/injury. The device or system can also be used for measuring concentrations of optically active carbohydrates, such as blood sugar (glucose), which helps in determining the glycemic condition of a person and their probability of becoming diabetic.

The present disclosure measures the analyte concentration using a non-invasive method using optical reflection spectroscopy and optical absorption. The present invention is rapid as the method is passive and analyte is not excited optically. This method may be reliable for diagnosis and does not require any baseline measurements. In addition, a broad spectrum primarily in the visible light range is used and hence the device is cost effective, and easy to operate. Further, the system or device can be integrated with an eyewear such a spectacles or sunglasses.

Although the present invention has been described through the use of exemplary embodiments, it will be appreciated by those of skill in the art that various modifications may be made to the described embodiments that fall within the scope and spirit of the invention as defined by the claims and their equivalents appended hereto.

What is claimed is:

1. A device for measuring an analyte concentration level in a subject, the device comprising:
 a light source configured for illuminating at least a portion of an anterior region of an eye of the subject with incident light having a substantially broad illumination spectrum at an angle substantially tangential to the surface of the eye;
 an optical collector configured for detecting at least one of scattered or reflected light from the at least a portion of the anterior region of the eye;
 an analyzer configured for analyzing the detected at least one of scattered or reflected light; and
 a processor configured to determine the analyte concentration level in the subject based on the analyzed at least one of scattered or reflected light.

2. The device of claim 1, wherein the processor determines a health condition of the subject based on the analyte concentration level and reference data, and wherein the reference data corresponds to an analyte concentration level in an anterior region of a healthy eye.

3. The device of claim 1, wherein the illumination spectrum comprises wavelengths ranging from about 200 nm to about 900 nm.

4. The device of claim 1, wherein the angle at which the eye is illuminated ranges from about 70 degrees to about 90 degrees.

5. The device of claim 1, further comprising a modulator configured for modulating the incident light to reduce extraneous effects.

6. The device of claim 1, wherein the analyzer comprises an optical spectrometer.

7. The device of claim 1, wherein the analyzer comprises an interferometer.

8. The device of claim 1, wherein the light source comprises an incoherent light source.

9. The device of claim 1, wherein the analyte concentration level measured is of an analyte comprising at least one of metabolic compounds selected from the group consisting of: carbohydrates, sodium, sodium based salts, sugars, glucose, proteins, peptides, amino acids, fats, fatty acids, triglycerides, polysaccharides, alcohols, ethanol, toxins, hormones, vitamins, bacteria-related substances, fungus-related substances, virus-related substances, parasite-related substances, pharmaceutical compounds, non-pharmaceutical compounds, pro-drugs, drugs, precursors, metabolites, degradation products, biomarkers, and surrogate markers.

10. A method for measuring an analyte concentration level in a subject, the method comprising:
 irradiating at least a portion of an anterior region of an eye with incident light having a substantially broad illumination spectrum at an angle substantially tangential to the surface of the eye;
 detecting at least one of scattered or reflected light from the at least a portion of the anterior region;
 analyzing the at least one of scattered or reflected light; and
 determining the analyte concentration level based on the analyzed at least one of scattered or reflected light.

11. The method of claim 10, further comprising determining a health condition of the subject based the analyte concentration level and reference data, wherein the reference data corresponds to an analyte concentration level in the anterior region of a healthy eye.

12. The method of claim 10, wherein the illumination spectrum comprises wavelengths ranging from about 200 nm to about 900 nm.

13. The method of claim 10, further comprising modulating the incident light to reduce extraneous effects.

14. The method of claim 10, wherein the analyte concentration level measured is of an analyte comprising at least one metabolic compound selected from the group consisting of: carbohydrates, sodium, sodium based salts, sugars, glucose, proteins, peptides, amino acids, fats, fatty acids, triglycerides, polysaccharides, alcohols, ethanol, toxins, hormones, vitamins, bacteria-related substances, fungus-related substances, virus-related substances, parasite-related substances, pharmaceutical compounds, non-pharmaceutical compounds, pro-drugs, drugs, precursors, metabolites, degradation products, biomarkers, and surrogate markers.

15. A device for measuring an analyte concentration level in a subject, the device comprising:
 a light source configured for illuminating at least a portion of an anterior region of an eye of the subject with incident light having a substantially broad illumination spectrum at an angle substantially tangential to the surface of the eye;
 an optical splitter configured for splitting the incident light into first polarized rays and second polarized rays, wherein a polarization of the first polarized rays is substantially perpendicular to a polarization of the second polarized rays;
 a first polarization rotation element configured for rotating the polarization of the first polarized rays to be substantially parallel to the polarization of the second polarized rays;
 a first variable rotator configured for rotating the polarization of the first polarized rays and the polarization of the second polarized rays;
 a second variable rotator configured for rotating a polarization of first reflected rays and a polarization of second reflected rays, wherein the first reflected rays and the second reflected rays comprise at least one of scattered or reflected light reflected from the at least a portion of the anterior region of the eye;
 a second polarization rotation element configured for rotating the polarization of the second reflected rays to be substantially perpendicular to the polarization of the first reflected rays;
 an optical combiner configured for combining the first and second reflected rays into combined reflected rays;
 an optical collector configured for detecting the combined reflected rays;
 an analyzer configured for analyzing the combined reflected rays; and
 a processor configured to determine the analyte concentration level in the subject based on the analyzed combined reflected rays.

16. The device of claim 15, wherein the processor determines a health condition of the subject based on the analyte concentration level and reference data, and wherein the reference data corresponds to an analyte concentration level in an anterior chamber of a healthy eye.

17. The device of claim 15, wherein the illumination spectrum comprises wavelengths ranging from about 200 nm to about 900 nm.

18. The device of claim 15, wherein the angle at which the eye is illuminated ranges from about 70 degrees to about 90 degrees.

19. The device of claim 15, wherein a path length of the second polarized rays and a path length of the second reflected rays in the aqueous humor is greater than a path length of the first polarized rays and a path length of the first reflected rays, respectively, in the aqueous humor.

20. The device of claim 15, wherein the analyte concentration level measured is of an analyte comprising at least one of metabolic compounds selected from the group consisting of: carbohydrates, sodium, sodium based salts, sugars, glucose, proteins, peptides, amino acids, fats, fatty acids, triglycerides, polysaccharides, alcohols, ethanol, toxins, hormones, vitamins, bacteria-related substances, fungus-related substances, virus-related substances, parasite-related substances, pharmaceutical compounds, non-pharmaceutical compounds, pro-drugs, drugs, precursors, metabolites, degradation products, biomarkers, and surrogate markers.

* * * * *